United States Patent [19]

Böger et al.

[11] 4,379,147
[45] Apr. 5, 1983

[54] SUBSTITUTED 2-(ANILINOMETHYL)-2-IMIDAZOLINE DERIVATIVES, COMPOSITIONS CONTAINING THESE DERIVATIVES, AND THE USE THEREOF FOR COMBATING PESTS

[75] Inventors: Manfred Böger, Weil am Rhein, Fed. Rep. of Germany; Urs Burckhardt, Basel, Switzerland; Haukur Kristinsson, Bottmingen, Switzerland; Günter Mattern, Liestal, Switzerland; Walter Traber, Reinach, Switzerland

[73] Assignee: Ciba-Geigy Corporation, Ardsley, N.Y.

[21] Appl. No.: 344,280

[22] Filed: Feb. 1, 1982

[30] Foreign Application Priority Data

Feb. 9, 1981 [CH] Switzerland ..................... 842/81

[51] Int. Cl.³ ..................... A01N 57/32; C07F 9/24
[52] U.S. Cl. ..................... 424/200; 548/111
[58] Field of Search ..................... 548/111; 424/200

[56] References Cited

FOREIGN PATENT DOCUMENTS

| 1647 | 5/1979 | European Pat. Off. . |
| 2756638 | 6/1978 | Fed. Rep. of Germany . |
| 2756639 | 6/1978 | Fed. Rep. of Germany . |
| 2023603 | 1/1980 | United Kingdom . |

*Primary Examiner*—Robert W. Ramsuer
*Attorney, Agent, or Firm*—Frederick H. Rabin

[57] ABSTRACT

Compounds of the formula

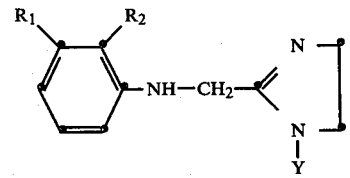

wherein $R_1$ and $R_2$ independently of one another are each a chlorine atom or the methyl group, Y is the group

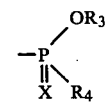

or $-CH=N-R_5$, in which $R_3$ is methyl or ethyl, $R_4$ is alkyl having 1 to 4 carbon atoms, alkoxy having 1 or 2 carbon atoms, alkylthio having 1 to 4 carbon atoms, or phenyl, X is an oxygen atom or a sulfur atom, and $R_5$ is an unsubstituted or substituted pyridinyl group which is linked by way of one of its carbon atoms, to the main part of the molecule, and which has substituents selected from the group comprising halogen and alkyl having 1 to 4 carbon atoms, including the acid addition salts thereof, processes for producing the novel compounds by reaction of 2-(anilinomethyl)-2-imidazoline derivatives either with (thio)phosphoric acid dialkyl ester halides or alkyl(thio) phosphonic acid alkyl ester halides, or with N-pyridinylformiminoalkoxy derivatives. The resulting compounds and compositions containing them are effective against members of the order Acarina, and against animal and plant lice, as well as against members of the Calliphoridae family.

12 Claims, No Drawings

SUBSTITUTED 2-(ANILINOMETHYL)-2-IMIDAZOLINE DERIVATIVES, COMPOSITIONS CONTAINING THESE DERIVATIVES, AND THE USE THEREOF FOR COMBATING PESTS

The present invention relates to novel substituted 2-(anilinomethyl)-2-imidazoline derivatives, to processes for producing them, to pesticidal compositions containing the said derivatives as active ingredients, and to methods for combating pests by application of the novel compounds.

2-(Anilinoalkyl)-2-imidazoline derivatives exhibiting pesticidal, particularly ectoparasiticidal, activity are known (cp. for example British Patent Specification No. 2,023,603, European Patent Specification No. 0,001,647 and German Offenlegungsschriften Nos. 2,756,638 and 2,756,639). There are provided with the present invention novel compounds of this type which have a pronounced action against pests, especially against members of the order Acarina, and which are particularly suitable for practical application by virtue of their advantageous biological properties.

The novel substituted 2-(anilinomethyl)-2-imidazoline derivatives according to the invention correspond to the formula I

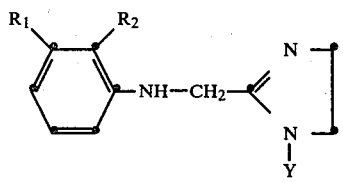

wherein
$R_1$ and $R_2$ independently of one another are each a chlorine atom or the methyl group,
Y is the group

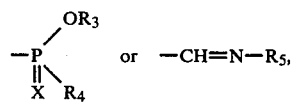

wherein
$R_3$ is methyl or ethyl,
$R_4$ is alkyl having 1 to 4 carbon atoms, alkoxy having 1 or 2 carbon atoms, alkylthio having 1 to 4 carbon atoms, or phenyl,
X is an oxygen atom or a sulfur atom, and
$R_5$ is an unsubstituted or substituted pyridinyl group which is linked by way of one of its carbon atoms to the main part of the molecule, and which has substituents selected from the group comprising halogen and alkyl having 1 to 4 carbon atoms;
and the present invention includes also the acid addition salts of these compounds.

Structurally, the compounds of the formula I embrace phosphorus-containing derivatives

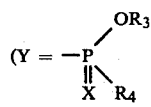

and pyridinylimine derivatives (Y=—CH=N—$R_5$).

The alkyl and alkylthio groups denoted by $R_4$ are: the methyl, ethyl, n-propyl, iso-propyl, n-butyl, iso-butyl, sec-butyl or tert-butyl group, as well as the methylthio, ethylthio, n-propylthio, iso-propylthio, n-butylthio, iso-butylthio, sec-butylthio or tert-butylthio group.

By alkyl groups as substituents of the pyridinyl group $R_5$ are meant the methyl, ethyl, n-propyl, iso-propyl, n-butyl, iso-butyl, sec-butyl and tert-butyl groups; and by halogen are meant fluorine, chlorine, bromine and iodine, preferably chlorine or bromine.

The compounds of the formula I are in the form of free bases or in the form of acid addition salts, for example mineral salts, and can be used according to the invention in both forms.

It has now been shown that the compounds of the formula I according to the invention surprisingly have a pronounced action against plant-damaging members of the order Acarina (for example mites of the families: Tarsonemidae, Erophyidae, Tyroglyphidae, Glycyphagidae and particularly Tetranychidae), and also against ectoparasitic members of this order (for example mites and ticks of the families: Sarcoptidae, Dermanyssidae, Ixodidae and Argasidae), which can seriously harm productive animals, and against members of the orders Phthiraptera (animal lice) and Phytophthires (plant lice), as well as against Diptera, which belong to the Calliphoridae family. To be mentioned as member of the Calliphoridae family is in particular the genus Lucilia, including especially the species *Lucilia sericata* (blowfly).

The compounds according to the invention are able, when applied to plants, to penetrate through the surface of the leaf into the inside of the leaves. The compounds of the formula I, with the inclusion of their acid-addition salts nontoxic to warm-blooded animals, are particularly suitable therefore for combating sucking plant pests, especially phytoparasitic members of the order Acarina, in crops of productive plants and ornamental plants, especially in fruit and vegetable crops, and in particular in the case of citrus cultivation.

To be emphasised in the zooparasitic field is especially the combating of ectoparasitic mites on productive animals, with particular reference being made in this respect to ticks as a subgroup of mites.

The effectiveness against pests is coupled with a low level of toxicity to warm-blooded animals, which is favourable for practical application, so that the compounds of the formula I and their acid addition salts nontoxic to warm-blooded animals are particularly suitable for combating pests of the order Acarina in crops of productive plants and ornamental plants, as well as for combating ectoparasitic ticks and mites on productive animals.

Preferred among the compounds of the formula I, in the phosphoric ester series, are those compounds, including the acid addition salts thereof, in which X is oxygen, $R_3$ is ethyl, $R_4$ is alkylthio having 3 or 4 carbon atoms, and $R_1$ and $R_2$ have the meanings defined under the formula I. Of the formamidines of the formula I, however, preferred compounds, including the acid addition salts thereof, are those wherein $R_5$ is an unsubstituted or methylsubstituted pyridinyl group linked in the 2-position to the main part of the molecule, and $R_1$ and $R_2$ have the meanings defined under the formula I.

The following compounds, including their acid addition salts, are to be considered as being particularly preferred by virtue of their effectiveness:

1-(O-ethyl-S-sec-butyl-thiophosphonyl)-2-(2′,3′-dimethylanilinomethyl)-2-imidazoline, 1-(O-ethyl-S-isobutyl-thiophosphonyl)-2-(2′,3′-dimethylanilinomethyl)-2-imidazoline, 1-(O-ethyl-S-n-propyl-thiophosphonyl)-2-(2′,3′-dimethylanilinomethyl)-2-imidazoline, 1-(O-ethyl-ethyl-thiophosphinyl)-2-(2′,3′-dimethylanilinomethyl)-2-imidazoline, 1-(O-ethyl-S-isobutylthiophosphonyl)-2-(2′,3′-dichloroanilinomethyl)-2-imidazoline, 1-(O-ethyl-S-n-propylthiophosphonyl)-2-(2′,3′-dichloroanilinomethyl)-2-imidazoline, 1-(O-ethyl-S-n-propyl-thiophosphonyl)-2-(2′-methyl-3′-chloroanilinomethyl)-2-imidazoline, 1-(O-ethyl-S-sec-butyl-thiophosphonyl)-2-(2′-methyl-3′-chloroanilinomethyl)-2-imidazoline, N-([2-(2,3-dimethylanilinomethyl)-2-imidazolin-1-yl]-methylidene)-N-(6-methylpyridin-2-yl)-imine, N-([2-(2,3-dimethylanilinomethyl)-2-imidazolin-1-yl]-methylidene)-N-(pyridin-2-yl)-imine, N-([2-(2,3-dichloroanilinomethyl)-2-imidazolin-1-yl]-methylidene)-N-(pyridin-2-yl)-imine, N-([2-(2,3-dichloroanilinomethyl)-2-imidazolin-1-yl]-methylidene)-N-(3-methylpyridin-2-yl)-imine, N-([2-(2,3-dichloroanilinomethyl)-2-imidazolin-1-yl]-methylidene)-N-(6-methylpyridin-2-yl)-imine, and N-([2-(2,3-dichloroanilinomethyl)-2-imidazolin-1-yl]-methylidene)-N-(4-methylpyridin-2-yl)-imine.

The compounds of the formula I are produced, using known processes, by for example reacting a compound of the formula II

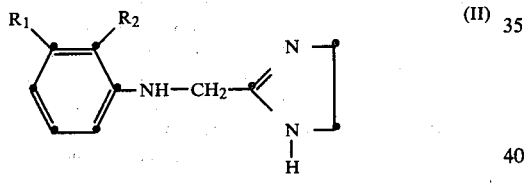

(a) with a compound of the formula IIIa

$R_1$, $R_2$, $R_3$, $R_4$ and X in the formulae II and IIIa having the meanings defined under the formula I, and "Hal" being a halogen atom, especially a chlorine or bromine atom, at a temperature of between $-20°$ and $80°$ C. under normal or slightly elevated pressure, in the presence of a base and preferably in a solvent or diluent inert to the reactants; and (b) with a compound of the formula IIIb

$R_1$, $R_2$ and $R_5$ in the formulae II and IIIb having the meanings defined under the formula I, and $R_6$ being methyl or ethyl, at a temperature of between $-20°$ and $120°$ C., under normal or slightly elevated pressure, and preferably in a solvent or diluent inert to the reactants.

Suitable solutions or diluents for use in the reactions described in the foregoing are for example: ethers and ethereal compounds, such as diethyl ether, diisopropyl ether, dioxane and tetrahydrofuran; aromatic hydrocarbons, such as benzene, toluene and xylenes; and ketones, such as acetone, methyl ethyl ketone and cyclohexanone.

Suitable bases are in particular: tertiary amines, such as trialkylamines, pyridines and dialkylanilines, also hydroxides, oxides, carbonates and bicarbonates of alkali metals and alkaline-earth metals, as well as alkali metal alcoholates, for example potassium tert-butylate and sodium methylate.

The compounds of the formula I produced in this manner can be converted into their acid salts by methods known per se.

The starting materials used in the aforementioned reactions are known (cp. German Offenlegungsschriften Nos. 2,750,902 and 2,756,638), or can be produced by methods analogous to known methods.

EXAMPLE 1

Production of
1-(O-ethyl-S-n-propyl-thiophosphonyl)-2-(2′,3′-dimethylanilinomethyl)-2-imidazoline To a suspension of 8.1 g of 2-(2′,3′-dimethylanilinomethyl)-2-imidazoline in 100 ml of toluene at 0° to 10° C. are added 4.3 g of triethylamine, and subsequently is added dropwise at 0° to 16° C., with continuous stirring, a solution of 8.1 g of O-ethyl-S-n-propyl-thiochlorophosphate in 50 ml of toluene. The reaction mixture obtained is stirred for one hour at about 10° C.; 100 ml of water are then added, and the toluene phase is repeatedly washed with a small amount of water. After evaporation of the previously dried toluene solution and drying at 50° C. under high vacuum, there is obtained the compound of the formula

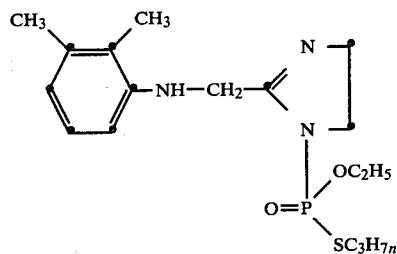

in the form of clear yellow oil having a refractive index of $n_D^{20}=1.5601$.

EXAMPLE 2

N-([2-(2,3-Dimethylanilinomethyl)-2-imidazolin-1-yl]-methylidene)-N-(3-methylpyridin-2-yl)-imine 8.0 g of 2-(2,3-dimethylanilinomethyl)-2-imidazoline and 6.6 g of N-(3-methylpyridin-2-yl)-formiminoethyl ether of the formula IV

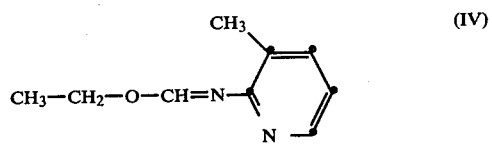

are stirred with 100 ml of toluene for 5 hours at a temperature of 70° C. The reaction mixture obtained is concentrated by evaporation, and the residue is recrystallised twice from toluene to thus obtain N-([2-(2,3- dimethylanilinomethyl)-2-imidazolin-1-yl]-methylidene)-N-(3-methylpyridin-2-yl)-amine of the formula V

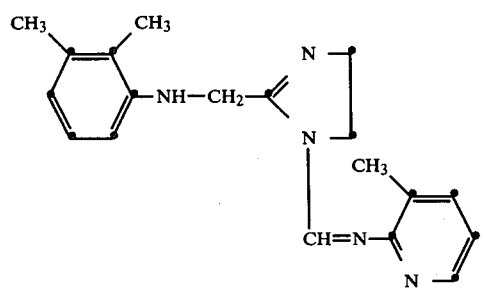

in the form of beige-coloured powder; m.p. 176°–178° C.

The following compounds of the formula I are produced in an analogous manner:

TABLE Ia

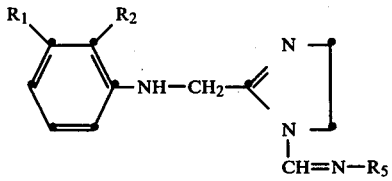

| No. | R₁ | R₂ | R₃ | R₄ | X | Physical data |
|---|---|---|---|---|---|---|
| 1a | CH₃ | CH₃ | C₂H₅ | S—CH(CH₃)—CH₂—CH₃ | O | $n_D^{20}$ 1,5510 |
| 2a | CH₃ | CH₃ | C₂H₅ | S—CH₂—CH(CH₃)₂ | O | $n_D^{20}$ 1,5516 |
| 3a | CH₃ | CH₃ | C₂H₅ | S—CH₂—CH₂—CH₃ | S | m.p. 59–61° C. |
| 4a | CH₃ | CH₃ | C₂H₅ | S—CH₂—CH₂—CH₃ | O | $n_D^{20}$ 1,5601 |
| 5a | CH₃ | CH₃ | C₂H₅ | C₂H₅ | S | highly viscous |
| 6a | CH₃ | CH₃ | C₂H₅ | O—C₂H₅ | O | $n_D^{20}$ 1,5332 |
| 7a | CH₃ | CH₃ | C₂H₅ | C₆H₅ | S | $n_D^{20}$ 1,6073 |
| 8a | CH₃ | CH₃ | CH₃ | O—CH₃ | O | $n_D^{20}$ 1,5440 |
| 9a | Cl | Cl | C₂H₅ | S—CH₂—CH(CH₃)₂ | O | $n_D^{20}$ 1,5656 |
| 10a | Cl | Cl | C₂H₅ | S—CH(CH₃)—CH₂—CH₃ | O | $n_D^{20}$ 1,5639 |
| 11a | Cl | Cl | C₂H₅ | S—CH₂—CH₂—CH₃ | O | $n_D^{20}$ 1,5743 |
| 12a | Cl | Cl | C₂H₅ | S—CH₂—CH₂—CH₃ | S | $n_D^{20}$ 1,6010 |
| 13a | Cl | Cl | C₂H₅ | O—C₂H₅ | O | $n_D^{20}$ 1,5505 |
| 14a | Cl | Cl | CH₃ | O—CH₃ | O | m.p. 92–94° C. |
| 15a | Cl | Cl | C₂H₅ | C₆H₅ | S | $n_D^{20}$ 1,6230 |
| 16a | Cl | CH₃ | C₂H₅ | S—CH₂—CH₂—CH₃ | O | oil |
| 17a | Cl | CH₃ | C₂H₅ | S—CH(CH₃)—CH₂—CH₃ | O | oil |

TABLE Ib

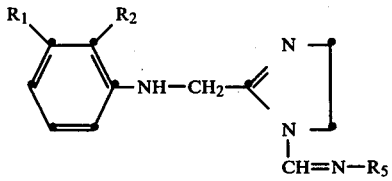

| No. | R₁ | R₂ | R₅ | m.p. °C. |
|---|---|---|---|---|
| 1b | CH₃ | CH₃ | 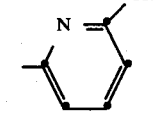 | 173–175 |
| 2b | CH₃ | CH₃ | 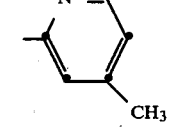 | 193–195 |
| 3b | CH₃ | CH₃ | 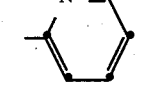 | 194–196 |
| 4b | CH₃ | CH₃ | 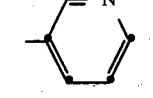 | 181–183 |
| 5b | CH₃ | CH₃ | 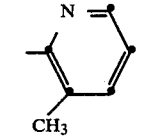 | 176–178 |
| 6b | Cl | Cl | 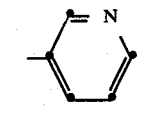 | 172–174 |
| 7b | Cl | Cl | 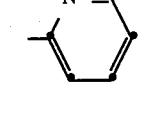 | 193–195(D) |
| 8b | Cl | Cl | 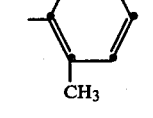 | 175–177 |
| 9b | Cl | Cl | 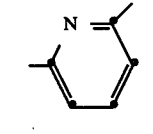 | 169–173 |
| 10b | Cl | Cl | 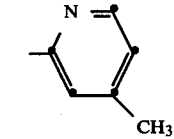 | 202–204 |

TABLE Ib-continued

R₁, R₂ substituted compound with NH—CH₂— linkage to a triazole bearing CH=N—R₅

| No. | R₁ | R₂ | R₅ | m.p. °C. |
|---|---|---|---|---|
| 11b | Cl | CH₃ | 6-methyl-2-pyridyl | |
| 12b | Cl | CH₃ | 2-pyridyl | |

The compounds of the formula I are used as such according to the invention, or they form a constituent of compositions containing in addition suitable carriers or additives, or mixtures of such substances. Suitable carriers and additives can be solid or liquid and they correspond to the substances common in formulation practice, for example natural or regenerated substances, solvents, dispersing agents, wetting agents, adhesives, thickeners, binders and/or fertilisers.

The acaricidal action of the compositions according to the invention can be broadened by the addition of other acaricides and/or insecticides. Suitable additives are for example: organic phosphorus compounds; nitrophenols; formamidines; ureas; pyrethrin-like compounds; carbamates and chlorinated hydrocarbons.

Representatives of the classes of substances referred to as additives to the compositions according to the invention are for example the following compounds:

O-(2-chloro-1-(2,4-dichlorophenyl)-vinyl)-O,O-diethylphosphate,
O,O-diethyl-O-(2-isopropyl-6-methyl-pyrimidin-4-yl)-phosphothionate,
cis-O,O-dimethyl-O-(2-dimethylcarbamoyl-1-methyl-vinyl)-phosphate,
N'-(4-chloro-o-toluene)-N,N-dimethylformamidine,
N-methyl-bis-(2,4-xyliminomethyl)-amine,
N-(2-methyl-4-chlorophenyl)-N',N'-dimethylthiourea,
2-(2',4'-dimethylphenylimino)-3-methyl-thiazoline,
3-methyl-5-isopropylphenyl-N-methyl-N-n-butanoyl-carbamate,
2-isopropoxyphenyl-N-methylcarbamate,
(+)-3-(2,2-dichlorovinyl)-2,2-dimethyl-cyclopropanecarboxylic acid-(α-cyano-3-phenoxybenzyl) ester,
(S)-α-cyano-3-phenoxybenzyl(1R)-cis-3-(2,2-dibromovinyl-2,2-dimethylcyclopropanecarboxylic acid ester,
(1R)-cis-3-(2,2-dibromovinyl)-2,2-dimethyl-cyclopropanecarboxylic acid-(S)-(α-cyano-3-phenoxybenzyl) ester, as well as the compound of the formula:

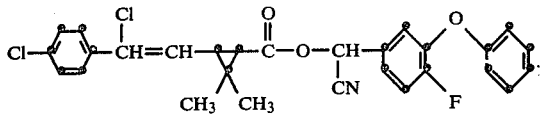

The compositions according to the invention can be for example in the form of dusts, granulates, dispersions, solutions and suspensions, and also in the form of water-dispersible wettable powders, pastes, emulsions and emulsion concentrates.

The content of active substance (compound of the formula I) in the compositions described above is between 0.1 and 95%; it is to be mentioned in this respect that, with application by means of suitable devices, also higher concentrations can be used.

The active substances of the formula I can be formulated for example as follows:

Emulsion Concentrate I 20 parts by weight of the active ingredient are dissolved in
70 parts by weight of xylene, and to the solution are added
10 parts by weight of an emulsifying agent consisting of a mixture of an arylphenolpolyglycol ether and the calcium salt of dodecylbenzenesulfonic acid.

Water can be added in any proportion to the emulsion concentrate to form a milky emulsion.

Emulsion Concentrate II 5 to a maximum of 30 parts by weight of the active ingredient are dissolved at room temperature, with stirring, in
30 parts by weight of dibutylphthalate,
10 parts by weight of Solvent 200 (low-viscous, highly aromatic petroleum distillate),
15 to 35 parts by weight of Dutrex 238 FC (viscous highly aromatic petroleum distillate), and to the solution are added
10 parts by weight of an emulsifier mixture consisting of castor-oil polyglycol ether and the calcium salt of dodecylbenzenesulfonic acid.

The emulsion concentrate thus obtained produces milky emulsions in water.

Wettable Powder 5 to 30 parts by weight of the active ingredient are thoroughly mixed, in a mixing apparatus, with
5 parts by weight of an absorbing carrier material (finely dispersed silicic acid) and
55 to 80 parts by weight of a carrier material (bolus alba or kaolin) and a dispersing agent mixture consisting of
5 parts by weight of a sodium lauryl sulfonate and
5 parts by weight of an alkyl-aryl-polyglycol ether.

This mixture is ground to 5–15 μm in a dowelled disc mill or air-jet mill. The wettable powder thus obtained gives a good suspension in water.

Dust 5 parts by weight of the finely ground active ingredient are thoroughly mixed with
2 parts by weight of a precipitated silicic acid and
93 parts by weight of talc.

"Pour-on" Solution

| active ingredient | 30.0 g |
|---|---|
| sodium dioctylsulfosuccinate | 3.0 g |
| benzyl alcohol | 48.0 g |
| peanut oil | 19.8 g |
| | 100.8 g = 100 ml. |

The active substance is dissolved in the benzyl alcohol with stirring and if necessary with gentle heating. The sodium dioctylsulfosuccinate and the peanut oil are added to the solution and dissolved with heating and thorough stirring.

EXAMPLE 3

Action against plant-damaging acarides: *Tetranychus urticae* (OP-sensitive) and *Tetranychus cinnabarinus* (OP-tolerant)

The primary leaves of *Phaseolus vulgaris* plants are infested, 16 hours before the test for acaricidal action, with an infested piece of leaf from a mass culture of *Tetranychus urticae* (OP-sensitive) and *Tetranychus cinnabarinus* (OP-tolerant), respectively (tolerance is with respect to compatibility with Diazinon). The infested plants treated in this manner are sprayed dripping wet with test solutions containing 400 and 200 ppm, respectively, of the compound to be tested. An assessment is made after 24 hours and again after 7 days, by examination of the imagines and larvae (all mobile stages) under a binocular microscope, of the living and dead individuals. One plant is used per concentration and per test series. The plants are standing during the test in greenhouse compartments at 25° C.

The compounds of the formula I effect in this test at least a 90% mortality rate against individuals of the species *Tetranychus urticae* and *Tetranychus cinnabarinus*.

EXAMPLE 4

Actoion against ectoparasitic acarides (ticks)
*Rhipicephalus bursa* (imagines and larvae), *Amblyomma hebraeum* (♀ imagines, nymphs and larvae) and
*Boophilus microplus* (imagines, larvae - OP-sensitive and OP-tolerant)

The test objects used are larvae (in each case about 50), nymphs (in each case about 25) and imagines (in each case about 10) of the tick species *Rhipicephalus burse*, *Amblyomma hebraeum* and *Boophilus microplus*. The test insects are immersed for a short time in an aqueous emulsion or solution containing the compound to be tested at a suitable concentration of between 0.1 and 1000 ppm. The emulsions or solutions in the test tubes are then absorbed with cotton wool, and the wetted test insects are left in the test tubes treated in this manner. An evaluation of the mortality rate achieved at each concentration is made after 3 days for larvae and after 14 days for nymphs and imagines.

The compounds of the formula I effect in this test at least a 90% mortality rate against larvae, nymphs and imagines of the species *Rhipicephalus bursa* and *Amblyomma hebraeum*, and also against imagines and larvae (OP-resistant and OP-sensitive) of the species *Boophilus microplus*. The compounds Nos. 1a, 2a, 4a, 5a, 9a, 11a, 16a, 17a, 1b, 3b and 7b–10b are 100% effective.

What is claimed is:

1. A compound of the formula

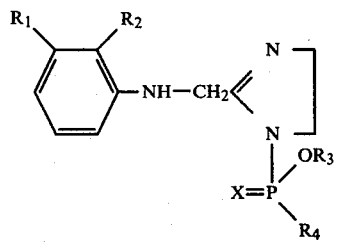

wherein
R₁ and R₂ independently of one another are each a chlorine atom or the methyl group,
R₃ is methyl or ethyl,
R₄ is alkyl having 1 to 4 carbon atoms, alkoxy having 1 or 2 carbon atoms, alkylthio having 1 to 4 carbon atoms, or phenyl, and
X is an oxygen atom or a sulfur atom, and
including acid addition salts thereof.

2. A compound according to claim 1, wherein R₃ is ethyl, R₄ is alkylthio having 3 or 4 carbon atoms, and X is an oxygen atom including acid addition salts thereof.

3. A compound selected from the group consisting of:

1-(O-ethyl-S-sec-butyl-thiophosphonyl-2-(2',3'-dimethylanilinomethyl)-2-imidazoline,
1-(O-ethyl-S-isobutyl-thiophosphonyl-2-(2',3'-dimethylanilinomethyl)-2-imidazoline,
1-(O-ethyl-S-n-propyl-thiophosphonyl-2-(2',3'-dimethylanilinomethyl)-2-imidazoline,
1-(O-ethyl-ethyl-thiophosphinyl-2-(2',3'-dimethylanilinomethyl)-2-imidazoline,
1-(O-ethyl-S-isobutylthiophosphonyl-2-(2',3'-dichloroanilinomethyl)-2-imidazoline,
1-(O-ethyl-S-n-propylthiophosphonyl-2-(2',3'-dichloroanilinomethyl)-2-imidazoline,
1-(O-ethyl-S-n-propyl-thiophosphonyl-2-(2'-methyl-3'-chloroanilinomethyl)-2-imidazoline, and
1-(O-ethyl-S-sec-butyl-thiophosphonyl-2-(2'-methyl-3'-chloroanilinomethyl)-2-imidazoline.

4. The compound according to claim 3 which is 1-(O-ethyl-S-sec-butyl-thiophosphonyl-2-(2',3'-dimethylanilinomethyl)-2-imidazoline.

5. The compound according to claim 3 which is 1-(O-ethyl-S-isobutyl-thiophosphonyl-2-(2',3'-dimethylanilinomethyl)-2-imidazoline.

6. The compound according to claim 3 which is 1-(O-ethyl-S-n-propyl-thiophosphonyl-2-(2',3'-dimethylanilinomethyl)-2-imidazoline.

7. A pesticidal composition comprising (1) a pesticidally effective amount of a compound according to claim 1 and (2) a carrier.

8. A method for combating pests which comprises applying thereto a pesticidally effective amount of a compound according to claim 1.

9. A method according to claim 8, whereby the pests are representatives of the order Acarina.

10. A method according to claim 8, whereby the pests are ectoparasites.

11. A method according to claim 8, whereby the pests are members of the orders Phthiraptera and Phytophthires.

12. A method according to claim 8, whereby the pests are members of the family Calliphoridae.

* * * * *